(12) United States Patent
Reedy et al.

(10) Patent No.: US 8,460,742 B2
(45) Date of Patent: Jun. 11, 2013

(54) METHOD OF DEVELOPING LATENT FINGERPRINTS

(75) Inventors: Brian Reedy, Ultimo (AU); Mark Tahtouh, Petersham (AU); Adam Brown, Meadowbank (AU); Di Fei Song, Sydney (AU); Daniel Sommerville, Bangor (AU); Ronald Shimmon, Greenfield Park (AU)

(73) Assignee: University of Technology, Sydney, Sydney (AU)

( * ) Notice: Subject to any disclaimer, the term of this patent is extended or adjusted under 35 U.S.C. 154(b) by 156 days.

(21) Appl. No.: 12/745,435

(22) PCT Filed: Nov. 28, 2008

(86) PCT No.: PCT/AU2008/001771
§ 371 (c)(1),
(2), (4) Date: Nov. 29, 2010

(87) PCT Pub. No.: WO2009/067761
PCT Pub. Date: Jun. 4, 2009

(65) Prior Publication Data
US 2011/0076383 A1     Mar. 31, 2011

(30) Foreign Application Priority Data
Nov. 29, 2007   (AU) ................................ 2007906521

(51) Int. Cl.
*A61B 5/103*   (2006.01)
*A61B 5/117*   (2006.01)

(52) U.S. Cl.
USPC .............................................. 427/1

(58) Field of Classification Search
USPC .............................................. 427/1
See application file for complete search history.

(56) References Cited

U.S. PATENT DOCUMENTS

| 4,708,882 | A |   | 11/1987 | Asano et al. ....................... 427/1 |
| 5,221,627 | A | * | 6/1993 | Grigg et al. ..................... 436/89 |
| 5,342,645 | A | * | 8/1994 | Eisele et al. ..................... 427/1 |
| 6,127,189 | A | * | 10/2000 | Joullie et al. .................. 436/111 |
| 2002/0027605 | A1 |   | 3/2002 | Lee ............................. 348/294 |
| 2006/0114549 | A1 |   | 6/2006 | Seah et al. ..................... 359/326 |
| 2007/0026130 | A1 | * | 2/2007 | Arndt ............................. 427/1 |
| 2008/0020126 | A1 | * | 1/2008 | Arndt ............................. 427/1 |

OTHER PUBLICATIONS

Authorized Officer Michelle Wu, International Search Report; PCT/AU2008/001771, Feb. 13, 2009.

* cited by examiner

*Primary Examiner* — Kelly M Gambetta
(74) *Attorney, Agent, or Firm* — Sunstein Kann Murphy & Timbers LLP

(57) ABSTRACT

Latent fingerprints on a porous substrate such as paper are developed for viewing and recordal by applying heat to cause the fingerprint to be clearly viewed under radiation to cause the fingerprint to fluorescence (e.g. a few seconds heating with hot air or client contact with a heated device at around 260° C.) and viewing under e.g. light of 200 nm to 550 nm with a filter in the yellow to orange wavelength region. Alternatively more extended heating can render the fingerprint assemble under ultraviolet light, and under yet more extended heating permits viewing under white light.

18 Claims, 3 Drawing Sheets

A

B

Figure 1:
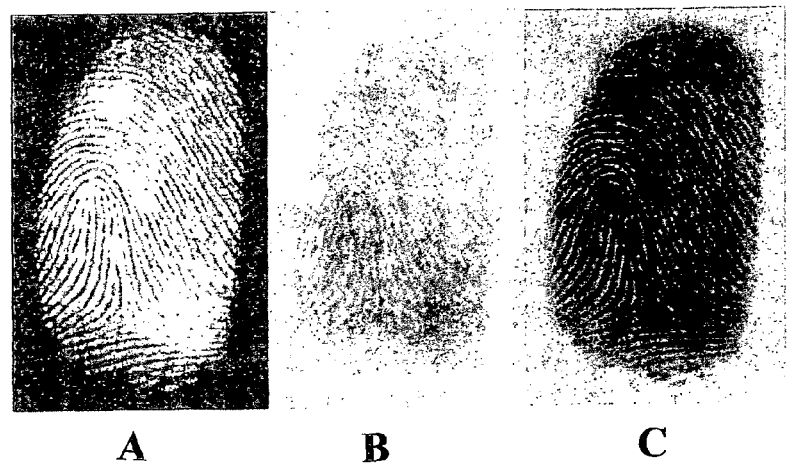

C 2 seconds 30 seconds 60 seconds 90 seconds 2 minutes 3 minutes 4 minutes

METHOD OF DEVELOPING LATENT FINGERPRINTS

TECHNICAL FIELD

This invention relates to a method of developing latent fingerprints and particularly to developing fingerprints on porous surfaces.

In this specification "porous surfaces or substrates" refers to paper, paper-like, other cellulose-based products (such as wood or other natural fibres, materials or fabrics such as cotton-based fabrics) and similar products, materials or fabrics susceptible to processing by the methods described herein.

BACKGROUND OF THE INVENTION

One known technique for detection of latent fingerprints on surfaces which may be porous (such as paper) is the use of optical imaging for example under ultraviolet light.

Another reported approach is to bake a sheet of paper carrying a latent fingerprint so as to develop an image.

Whereas such methods may be considered in some circumstances to have usefulness as a preliminary non-destructive testing technique, it is considered there are significant limitations and only poor results can be achieved with published methods.

Another known approach is to subject the substrate on which the fingerprint resides to a selected chemical treatment. Various reagents have been tried such as multi metal deposition (MMD) and amino acid sensitive reagents such as ninhydrin, 1,8-diazaflouroen-9-one (DFO) and 1,2-indanedione.

In referring to the above mentioned known techniques, no admission is made that any of these techniques are part of the common general knowledge in Australia or elsewhere.

It is considered that it would be desirable to have new and useful alternative techniques capable of embodiment in advantageous methods.

SUMMARY OF THE INVENTION

The present invention, in one aspect provides a method of developing for viewing latent fingerprints on a porous substrate including the steps of: exposing the substrate to heat to develop the fingerprint to a fluorescent stage, applying suitable frequency radiation to cause the fingerprint to fluoresce and viewing the fluorescing fingerprint.

Heating the fingerprint can be accomplished using convective heating, such as subjecting it to a hot gaseous medium such as heated air is one embodiment. Alternatively, the sample may be heated using conductive techniques such as to bring it into direct contact with a hot surface.

In general the area of the substrate carrying the fingerprint needs to be adequately uniformly raised in temperature for a time such that the fingerprint is developed to the fluorescent stage and can be seen in detail. In this embodiment but the temperature of the substrate should be constrained below a level at which excessive damage to the substrate and the fingerprint content occurs. With porous substrates such as paper, the requisite temperature band and time can be established by experiment and examples will be given hereinafter.

The method may further include the step of illuminating the surface with light in a selected frequency band to assist viewing, for example 200 nm to 550 nm to allow viewing of the induced fluorescence and more preferably 250 nm to 505 nm.

The method may further include the step of viewing the surface of the substrate through a filter to limit the illumination to a selected frequency band, for example using a filter in the yellow to orange portion of the spectrum, e.g. about 550 nm. Generally, a filter is used which permits only radiation of a longer wavelength than the radiation that is used to cause the sample to fluoresce.

In a second aspect, the invention consists in a method of developing a latent fingerprint on a porous substrate comprising applying heat to a sufficiently elevated temperature and for sufficient time to develop the fingerprint to be viewable under ultraviolet light, illuminating the fingerprint under ultraviolet light and viewing the fingerprint.

In a third aspect, the invention consists in a method of developing a latent fingerprint on a porous substrate comprising applying heat to a sufficiently elevated temperature and for sufficient time to develop the fingerprint to be viewable under white light, illuminating the fingerprint under white light and viewing the fingerprint.

The surface of the substrate generally is heated to between 180° C. and 400° C., such as to about 300° C. More generally, the medium for heating the substrate may be in the range of 200° C. to 300° C. and more preferably 230° C. to 300° C. e.g. about 280° C. During exposure to heat in general the substrate is unlikely to reach the temperature of the applied medium.

The surface of the substrate may be heated for between 1 seconds and 6 minutes, such as about 10 to about 20 seconds, but this could be a shorter time where the substrate is paper and the heating medium is over 230° C. For example heating in air for about 10 seconds will generally develop a fingerprint on paper to be viewed when fluorescent but 20 seconds will be needed to achieve viewing under white light. In an intermediate stage of development, the fingerprint may be viewable under fluorescent, and ultraviolet conditions.

The method may be implemented by viewing under white light or under fluorescent conditions, or under ultraviolet light.

Processing conditions may be otherwise controlled (e.g. to have a substantially oxygen-free zone for the substrate when heated).

Use of the invention is especially useful for developing fingerprints on porous surfaces such as paper.

In a further aspect the present invention consists in establishing fingerprint data comprising taking a fingerprint on a porous substrate, developing it in accordance with any one of the embodiments of the invention to render the fingerprint readily and accurately viewable and optionally recording the fingerprint with its analysis.

It will be appreciated that embodiments of the invention avoid destruction or contamination of the fingerprint or substrate due to reagents and a clean process is offered which can either be laboratory operated or operated in situ to permit the collection and preservation of evidence. The invention lends itself to be implemented into current forensic workflows, such that subsequent development techniques can be applied to a sample that has been developed using the techniques embodied in this invention. Embodiments include those which can be performed by operators who can quickly be trained and provide a simple, reliable and cost effective methodology for fingerprint acquisition and processing.

Embodiments of the invention facilitate a clean, rapid and reliable system for obtaining suitable specimens outside a laboratory and even permits reliable, portable processing without the use of laboratory conditions and expense.

Embodiments of the invention can offer several significant advantages, including:—
- simple equipment is used,
- the methodology can be inexpensively deployed with low levels of training,
- system is portable,
- no chemicals are required so that hazards are avoided,
- the test is non-destructive,
- other techniques may be used subsequently if required, including ninhydrin and DNA profiling,
- a useful, practical method is now provided for use on very difficult surface, namely paper and paper-like porous substrates.
- covert imaging of fingerprints is possible when samples are heated to the fluorescence stage only

DETAILED DESCRIPTION OF EXAMPLES

Several examples of the invention will now be described. All examples operate on the principle of applying heat to the surface of the substrate upon which a latent fingerprint has been deposited. The common features of the Examples will now be described.

In all the Examples, fingerprints were prepared and deposited on a range of porous surfaces (mostly paper) according to the following general method. The donors' hands were thoroughly washed, rinsed and dried before swiping a cleaned finger across an oily region of the face (forehead, nose or neck) and finally placing the mark on the desired surface. Samples were then treated within 48 hours. Aged samples were also prepared in the same manner and stored in paper envelopes in ambient conditions for the specified period.

During some experiments eccrine rich fingerprints were prepared by placing the cleaned hands of a donor in a latex powder free glove. The donor then undertook 5 minutes of vigorous exercise to produce sweaty hands before removing the glove and depositing a series of depleted prints on the desired surface. Eccrine rich fingerprints were compared with sebaceous rich fingerprints from the same donor (prepared using the general method described above). Little difference was found using methods according to examples of the invention.

Fingerprints from a range of randomly selected donors (5 male, 5 female) were also examined. For these experiments, the donors hands were not washed prior to the deposition of fingerprints as described above. Little difference was found with fingerprints developed according to examples of the invention.

Results were imaged by the Rofin Poliview IV® set up with Retiga 2000R CCTV camera, Rofin Polilight PL 500 and filters. Images were taken under one of the following conditions:

505 nm illumination with 550 nm high pass filter for fluorescent samples ultraviolet (350 nm) illumination with no filter for visible samples white light illumination with no filter for visible samples In the attached reproductions of photographs, fluorescent images were captured in this way.

The general result was that after a short heating time of typically 10 to 20 seconds, the (still invisible) fingerprint ridges fluoresced under 505 nm illumination and could be observed using a 550 nm filter. However, other embodiments can use other frequency illumination and/or other frequency filter.

Longer heating times generally led to dark brown-colored development of the fingerprint ridges, typically against a pale brown (scorched) background of the rest of the paper. At this stage, ridge contrast could be enhanced using ultraviolet illumination. Further heating caused loss of ridge contrast as all of the paper turned dark brown before it combusted or disintegrated. These stages of development mirror those of clean paper itself upon heating.

In contrast to Examples of the invention set out below, a comparative Example which was ineffective will now be first given.

COMPARATIVE EXAMPLE

Direct contact heating of a substrate used firstly a heating process (160° C. to 200° C.) and secondly a domestic iron (about 180° C.) to try and develop a latent fingerprint on paper. Despite extended contact times ineffective results were obtained and good contrast, useful, developed fingerprints were not obtained.

Example 1

Hot Air Gun

A hot air gun (Leister Triac S Hot Air Blower) was calibrated using a thermocouple to measure the temperature of the air emitted at two distances from the device, namely 3 cm and 6 cm, for ten different heat settings spanning the full range. This corresponded to a temperature range of 45-360° C. at 6 cm and 60-535° C. at 3 cm. These were air temperatures and it is likely that paper at these distances only approached but probably did not reach these temperatures.

At a heating distance of 6 cm, an air temperature of 160° C. did not give rise to any fluorescent or visible development of fingerprints on white copy paper after heating for 8 min. Fingerprint development started to be observed at temperatures above about 220° C., and at 245° C., fluorescent prints were developed after 6 min of heating. By 310° C., fluorescent fingerprints were developed after 45 sec, turning visible (brown) after about 1 min. This process accelerated with further increases in temperature (15 sec and 30 sec at 340° C.) but not surprisingly the paper quickly started to burn.

At a heating distance of 3 cm, the same temperatures could be achieved at lower heat gun settings, but the temperature of the substrate was more difficult to control. It was not possible at either heating distance to develop fingerprints that had been deposited on paper that was subsequently crumpled and smoothed out.

General drawbacks of the air gun were that it gave poor temperature resolution and uneven heat distribution, and therefore made the rate of heating difficult to control, so that the quality of fingerprint development was not very reproducible. Another disadvantage is that it can only be used to develop small areas of a page.

Example 2

Muffle Furnace

A wire embedded element furnace (made by B and L Tatlow) was used. The nominal temperature of the muffle furnace was set in the vicinity of 300° C.; monitoring of the actual temperature with a thermocouple showed that temperature variation was ±10° C. Since the door had to be opened to admit the sample, the "initial" temperature at which the paper sample was heated was generally 20-30° C. degree cooler than nominal. For an initial temperature of about 300° C., the times for fluorescent and then subsequent visible fingerprint development were 10 seconds and 20 seconds respectively. Some general observations were:

Visible prints could be developed on every type of paper tested, although the development of fluorescent prints prior to visible observation was not observed for some copy paper colors.

Using the furnace, fingerprints on crumpled paper could be developed.

One week-old and seven week-old prints could be developed in the furnace.

Example 3

GC Oven

A Hewlett Packard 5890 Series II Gas Chromotography (GC) oven was used. Samples (white copy paper) developed in the GC oven were subjected to a linear temperature ramp taking them from 100 to 300° C. at rates which varied from 5 degree C/min to 70 degrees C/min. All of these experiments were conducted until visible prints could be observed on the paper. In general, no visible prints were observed before 220° C., and the best prints were obtained with the fastest heating rate of 70 degrees C/min, although all of the ramps developed fingerprints.

A fingerprint aged for two months was also successfully developed in the GC oven.

Example 4

Direct Contact Heating

A heating block of metal attached to a soldering iron at about 300° C. was used. This did yield some fingerprint development, but with poor contrast due to scorching.

Example 5

Hair Straightener

A Remington Wet2Straight 230° C. hair straightener was pre-heated and its flat contact surfaces clamped over paper having latent fingerprints. The surfaces were measured at 230-236° C. A few seconds (e.g. 15 seconds) exposure to heat resulted in good contrast under fluorescent conditions when viewed under 505 nm illumination and 550 nm orange filter. When extended heat was applied, the fingerprints were visible under white light and with ultraviolet light at about 320 nm revealing good contrast with intermediate time.

After 30 seconds heating, fluorescence was still maintained.

FIG. 1 illustrates developed fingerprints on paper respectively:—A– under fluorescence, B– under white light and C– under ultraviolet light.

FIGS. 2-8 respectively show developments for fingerprints having different development times, in each case when examined under fluorescence (left hand photograph), ultraviolet light (middle photograph) and white light (right hand photograph).

Thus fluorescence was effective from 2 seconds to 90 seconds and ultraviolet from 30 seconds to 4 minutes whereas white light becomes viable at 2 minutes or more of heating.

It is suggested that development of a fingerprint is a function of temperature and time. However, it will be appreciated that other factors, such as the constituents of the donor fingerprint, the substrate, the age of the fingerprint, the mode of heating, and so on, will all contribute to the temperature and time necessary to cause an individual fingerprint to develop. It will also be appreciated that the parameters given to develop a fingerprint to the fluorescent stage may inform the operator as to subsequent development parameters for that sample.

Example 6

Figure 9:
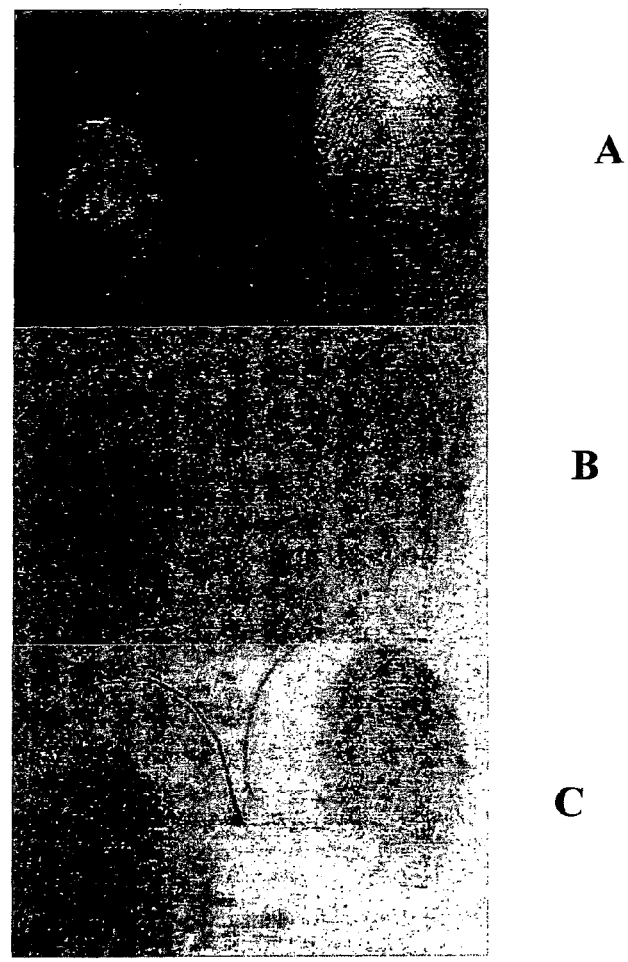
Figure 2:
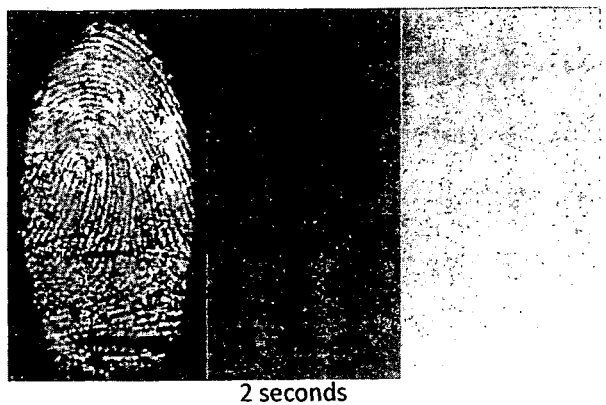
Figure 3:
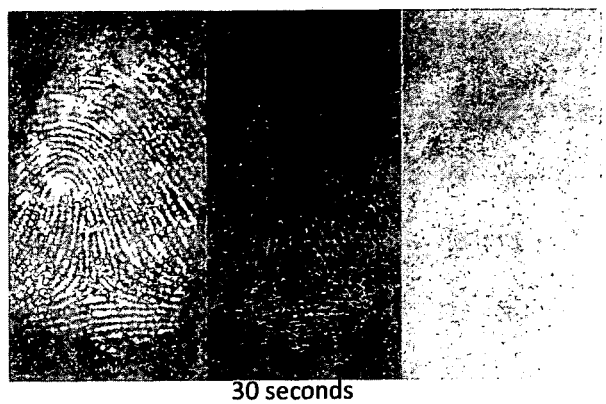
Figure 4:
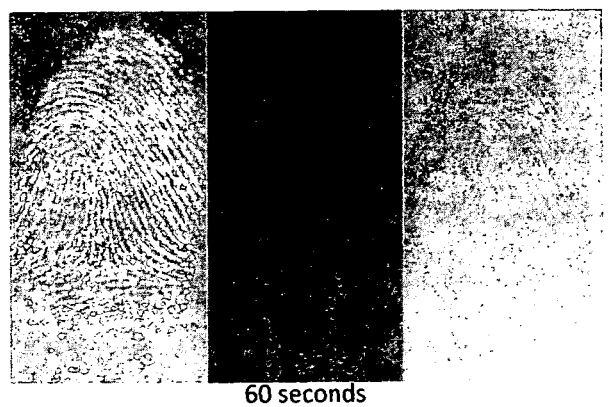
Figure 5:
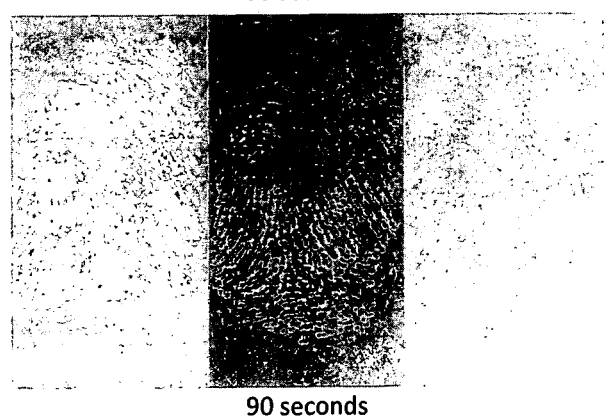
Figure 6:
Figure 7:
Figure 8:

Fingerprints on unpolished wood were developed using the technique of Example 5. FIG. 9 is a photograph of developed fingerprints respectively taken almost immediately after commencement of heating (visible in the view A under fluorescence) after extending heating (view B under visible light) and view C under ultraviolet light.

The invention claimed is:

1. A method of developing latent fingerprints on a porous substrate including the steps of
   exposing the substrate to heat in the absence of developing reagents to develop the fingerprint to a fluorescent stage; and
   applying suitable frequency radiation to cause the fingerprint to fluoresce and viewing the fluorescing fingerprint.

2. A method according to claim 1, wherein light in the range of about 200 nm to about 550 nm is used to cause fluorescence.

3. A method according to claim 2, wherein light in the range of 350 to 505 nm is used.

4. A method according to claim 1, including the step of viewing the fingerprint through a filter to limit viewing to a selected frequency band.

5. A method according to claim 4, wherein illumination is with light of about 500 nm wavelength and viewing is through a filter in the yellow or orange wavelength region.

6. A method according to claim 4, wherein the filter is about 550 nm.

7. A method according to claim 1, wherein the substrate is exposed to a temperature in the range of about 200° C. to about 300° C.

8. A method according to claim 7, wherein temperature is in the range of 230° C. to 300° C.

9. A method according to claim 8 wherein the substrate is exposed to a temperature of about 260° C.

10. A method according to claim 1, wherein the substrate is exposed for about 1 second to about 30 seconds.

11. A method according to claim 10, wherein the substrate is exposed for a few seconds.

12. A method according to claim 1, wherein heat is applied by direct contact heating with a heated device.

13. A method according to claim 1, and further comprising extending the time of exposure to heat to cause the fingerprint to be developed so that it is visible under ultraviolet light, and viewing the fingerprint under such light.

14. A method according to claim 1, comprising extending the exposure to heat to cause the fingerprint to be further developed to be viewed under white light.

15. A method according to claim 1, and further comprising optical recording and assessment of the fingerprint when developed.

16. A method of developing for viewing latent fingerprints on a porous substrate including the steps of
   exposing the substrate to heat by a direct contact method with a heated device at a temperature of about 230° C. to about 300° C. for a few seconds to cause the latent fingerprint to develop to a fluorescent stage; and illuminating the developed fingerprint with radiation of a suitable wavelength to cause fluorescence of the fingerprint, and viewing the fluorescent fingerprint.

17. A method as claimed in claim 16, wherein the heated device has two heated elements applied at about 260° C. to opposite sides of the substrate for a few seconds, and illumination is with light of about 350 to about 500 nm wavelength and viewing is via a filter in the yellow to orange portion of the spectrum.

18. A method of developing latent fingerprints on a porous substrate including the steps of:
  exposing the substrate to heat to develop the fingerprint to a fluorescent stage,
  applying suitable frequency radiation to cause the fingerprint to fluoresce and viewing the fluorescing fingerprint,
  wherein heat is applied in a hot gaseous medium modified relative to ambient atmosphere to alter the rate of development of the fingerprint and the gaseous medium is substantially inert and devoid of oxygen.

\* \* \* \* \*

UNITED STATES PATENT AND TRADEMARK OFFICE
CERTIFICATE OF CORRECTION

PATENT NO.       : 8,460,742 B2
APPLICATION NO.  : 12/745435
DATED            : June 11, 2013
INVENTOR(S)      : Reedy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this

Eighth Day of September, 2015

Michelle K. Lee
*Director of the United States Patent and Trademark Office*